US008845540B2

(12) United States Patent
Tsao et al.

(10) Patent No.: US 8,845,540 B2
(45) Date of Patent: Sep. 30, 2014

(54) ULTRASONIC DIAGNOSTIC APPARATUS FOR FORMING AN ULTRASOUND BEAM BASED ON A COMMON GROUPING PATTERN

(75) Inventors: Jing-Wen Tsao, Mitaka (JP); Takuya Kaneko, Mitaka (JP)

(73) Assignee: Hitachi Aloka Medical, Ltd., Tokyo (JP)

( * ) Notice: Subject to any disclaimer, the term of this patent is extended or adjusted under 35 U.S.C. 154(b) by 178 days.

(21) Appl. No.: 12/833,472

(22) Filed: Jul. 9, 2010

(65) Prior Publication Data

US 2011/0028846 A1    Feb. 3, 2011

(30) Foreign Application Priority Data

Jul. 28, 2009   (JP) ................................. 2009-175440

(51) Int. Cl.
*A61B 8/14*    (2006.01)
*G10K 11/34*   (2006.01)
*G01S 7/52*    (2006.01)
*G01S 15/89*   (2006.01)

(52) U.S. Cl.
CPC .............. *G10K 11/345* (2013.01); *A61B 8/14* (2013.01); *G01S 7/5208* (2013.01); *G01S 15/8925* (2013.01); *G01S 15/8927* (2013.01)
USPC ............................ 600/447; 600/437; 600/459

(58) Field of Classification Search
None
See application file for complete search history.

(56) References Cited

U.S. PATENT DOCUMENTS

| 5,229,933 | A | * | 7/1993 | Larson, III ..................... 600/459 |
| 5,563,346 | A | | 10/1996 | Bartelt et al. |
| 5,784,336 | A | * | 7/1998 | Gopinathan et al. .......... 367/123 |
| 5,997,479 | A | | 12/1999 | Savord et al. |
| 6,126,602 | A | | 10/2000 | Savord et al. |
| 6,868,729 | B2 | | 3/2005 | Amemiya |
| 7,090,642 | B2 | * | 8/2006 | Satoh ............................ 600/447 |

(Continued)

FOREIGN PATENT DOCUMENTS

| CN | 1575772 A | 2/2005 |
| EP | 0 430 450 A2 | 6/1991 |

(Continued)

OTHER PUBLICATIONS

European Search Report dated Nov. 30, 2010, issued in corresponding European Patent Application No. 10007109.1.

(Continued)

*Primary Examiner* — Long V. Le
*Assistant Examiner* — Bradley Impink
(74) *Attorney, Agent, or Firm* — Westerman, Hattori, Daniels & Adrian, LLP (57) ABSTRACT

A 2D array transducer (10) is separated into a plurality of sub-arrays. Four representative sub-arrays SA1 to SA4 are shown in an enlarged manner. In addition, the 2D array transducer (10) is segmented into a plurality of transducer regions. Four regions of (I)-(IV) segmented by dot-and-chain lines represent four transducer regions. A grouping process is executed for each sub-array to group the plurality of transducer elements belonging to the sub-array into a plurality of element groups. In this process, for each transducer region, a common grouping pattern is set for the plurality of sub-arrays belonging to the transducer region. For example, because sub-arrays SA1 and SA2 belong to the same transducer region (IV), a common grouping pattern is set for the sub-arrays SA1 and SA2.

14 Claims, 8 Drawing Sheets

(56) References Cited

U.S. PATENT DOCUMENTS

| | | | |
|---|---|---|---|
| 7,217,243 B2 | 5/2007 | Takeuchi | |
| 2004/0066708 A1* | 4/2004 | Ogawa | 367/138 |
| 2004/0267126 A1* | 12/2004 | Takeuchi | 600/447 |
| 2005/0243812 A1 | 11/2005 | Phelps | |
| 2006/0253034 A1 | 11/2006 | Fukukita | |
| 2008/0146930 A1* | 6/2008 | Takeuchi | 600/447 |
| 2008/0146938 A1* | 6/2008 | Hazard et al. | 600/462 |
| 2008/0234585 A1 | 9/2008 | Iwama | |
| 2008/0262351 A1 | 10/2008 | Scampini | |
| 2009/0306510 A1* | 12/2009 | Hashiba et al. | 600/447 |

FOREIGN PATENT DOCUMENTS

| | | | |
|---|---|---|---|
| EP | 1 936 404 A1 | 6/2008 | |
| JP | 61-52864 A | 3/1986 | |
| JP | 2-182245 A | 7/1990 | |
| JP | 4-254754 A | 9/1992 | |
| JP | 10-179585 A | 7/1998 | |
| JP | 2000-33087 A | 2/2000 | |
| JP | 2001-286467 A | 10/2001 | |
| JP | 2004-105257 A | 4/2004 | |
| JP | 2005-034633 A | 2/2005 | |
| JP | 2005-102717 A | 4/2005 | |
| JP | 2005-270423 A | 10/2005 | |
| JP | 2005-342194 A | 12/2005 | |
| JP | 3977827 B2 | 9/2007 | |
| JP | 2008-514335 A | 5/2008 | |
| JP | 2008-229096 A | 10/2008 | |
| WO | 2005-019856 A1 | 3/2005 | |
| WO | 2006-134686 A1 | 12/2006 | |
| WO | WO 2006134686 A1 * | 12/2006 | |

OTHER PUBLICATIONS

European Office Action dated Feb. 8, 2012, issued in corresponding European Patent Application No. 10007109.1, 6 pages.
Office Action dated Jul. 30, 2013, issued in corresponding Japanese application No. 2009-175440, with English Translation.
Office Action dated Feb. 19, 2013, issued in related Japanese Patent Application No. 2009-169817, with English translation (9 pages).
Office Action dated Mar. 29, 2013, issued in related Chinese Patent Application No. 201010234562.4; with English Translation (11 pages).
Office Action issued May 20, 2013 in corresponding Chinese Patent Application 201010238951.4 (11pages). English translation.
European Summons to attend oral proceedings pursuant to Rule 115(1) EPC dated Nov. 4, 2013, issued in corresponding European Patent Application No. 10006737.0, (5 pages).
European Decision to refuse a European Patent Application dated Feb. 21, 2014, issued in corresponding European Patent Application No. 10006737.0 (30 page).
European Provision of a copy of the minutes in accordance with Rule 124(4)EPC dated Feb. 21, 2014, issued in corresponding European Patent Application No. 10006737.0, (11 pages).
Chinese Office Action dated Dec. 12, 2013, issued in corresponding Chinese Patent Application No. 201010238951.4 with English translation(13 pages).
European Summons to attend oral proceedings pursuant to Rule 115(1) EPC dated Nov. 27, 2013, issued in corresponding European Patent Application No. 10007109.1(5 pages).
European Search Report dated Nov. 29, 2010, issued in corresponding European Patent Application No. 10006737.0 (8 pages).
Japanese Office Action dated Jul. 26, 2011, issued in corresponding Japanese Patent Application No. 2009-169817, with English translation (4 pages).
Office Action issued on Jul. 4, 2012 in corresponding Chinese Patent Application No. 201010234562.4, with English Translation (10 pages).
Office Action issued in European Patent Office on Nov. 22, 2011, in corresponding European Patent Application No. 10 006 737.0 (6 pages).
Chinese Office Action dated Aug. 30, 2012, issued in corresponding Chinese Patent Application No. 201010238951.4, with English translation (11 pages).
Final Office Action dated Jul. 5, 2012, Issued in U.S. Appl. No. 12/827,099 (14 pages).
Non-Final Office Action dated Jan. 9, 2012, issued in U.S. Appl. No. 12/827,099 (19 pages).
U.S. Non-Final Action dated Jun. 24, 2014, isssued in related U.S. Appl. No. 12/827,099 (38 pages).
Provision of the minutes in accordance with Rule 124(4)EPC dated May 23, 2014, issued in corresponding European Patent Application No. 10007109.1 (12 pages).
Decision to Refuse a European Patent Application dated May 23, 2014, issued in corresponding European Patent Application No. 10007109.1 (26 pages).

* cited by examiner

ULTRASONIC DIAGNOSTIC APPARATUS FOR FORMING AN ULTRASOUND BEAM BASED ON A COMMON GROUPING PATTERN

BACKGROUND

1. Technical Field

The present invention relates to an ultrasonic diagnostic apparatus, and, in particular, to a technique for forming an ultrasound beam using an array transducer.

2. Background Art

Two-dimensional array transducers constructed by two-dimensionally arranging a plurality of transducer elements are known. The two-dimensional array transducer is formed, for example, with a few thousand transducer elements which are electrically controlled. With the two-dimensional array transducer, ultrasound beams are two-dimensionally scanned, and echo data are three-dimensionally collected.

When a plurality of transducer elements which are a part of the two-dimensional array transducer are controlled, if a signal line is provided independently for each transducer element, a number of signal lines equaling the total number of transducer elements; for example, a few thousand signal lines, would be required for the overall two-dimensional array transducer. When a few thousand signal lines are employed, a probe cable connecting a probe in which the transducer elements are disposed and a device body would become thick, and the number of pins of the connector in a connection portion between the probe cable and the device body would also become large. In addition, the increase in circuit size for transmission/reception systems cannot be ignored. In consideration of these circumstances, techniques have been proposed for reducing the number of signal lines (number of channels) connecting the plurality of transducer elements and the device body.

For example, Patent Literature 1 (JP 2001-286467 A) discloses a technique in which a focus point of an ultrasound beam is projected onto an array transducer surface, a plurality of concentric rings are set centered at the projected point, and a common amount of delay is correlated to a plurality of transducer elements belonging to each concentric ring. With such a configuration, the number of channels can be significantly reduced to the number of concentric rings. However, a switching circuit for electrically collecting the plurality of transducer elements belonging to each concentric ring becomes very complex, and the amount of data for controlling the switching circuit also becomes very large.

Patent Literature 2 (JP 2005-342194 A) discloses a technique in which the two-dimensional array transducer is divided into a plurality of sub-arrays, and a plurality of transducers corresponding to the same amount of delay in each sub-array are connected (grouping). With the employment of the sub-array as in Patent Literature 2, although the number of channels is increased as compared with the case where the sub-array is not employed (for example, configuration in Patent Literature 1), the size of the switching circuit can be reduced as compared with such a case. However, the amount of data for controlling the switching circuit is still enormous.

In order to electrically collect a plurality of transducer elements by a switching circuit, for example, information for controlling the switching circuit is supplied from the device body to the probe. In order to control the switching circuit according to a steering angle of the beam and depth of focus, the amount of information to be supplied from the device body to the probe becomes very large. For example, when information related to a few thousand transducer elements is transferred, a transfer time of a few tens of microseconds would be required, resulting in other problems such as reduction in the frame rate.

Patent Literature 3 (JP 2000-33087 A) discloses a technique to apply a control such that the depth of focus is fixed at infinity and only the beam steering is considered, in order to simplify the beam control and reduce the amount of information. However, when the depth of the focus is simply set to infinity, converging of the beam etc. is degraded and the precision of the beamforming is reduced, resulting in reduction in resolution or the like of the image.

Under such circumstances, the present inventor have researched and developed a technique which inhibits degradation of the ultrasound beam while inhibiting an increase in the amount of information for controlling the ultrasound beam. In particular, the present inventors have focused attention on a grouping process for collecting a plurality of transducer elements of the array transducer into a plurality of element groups.

SUMMARY

The present invention is made in the above-described research and development process, and an advantage of the present invention is that an improved technique is provided in relation to a grouping process of an array transducer.

According to one aspect of the present invention, there is provided an ultrasound diagnostic apparatus comprising an array transducer comprising a plurality of transducer elements; a grouping processor which divides the array transducer into a plurality of sub-arrays and which groups, for each sub-array, a plurality of transducer elements belonging to the sub-array into a plurality of element groups; a controller which sets a grouping pattern defining a plurality of transducer elements to be grouped into a same element group; and a beam-forming unit which forms an ultrasound beam using a plurality of element groups grouped for each sub-array over the plurality of sub-arrays, wherein the array transducer is segmented into a plurality of transducer regions, and, for each transducer region, the controller sets a common grouping pattern for the plurality of sub-arrays belonging to the transducer region.

With the above-described configuration, because, for each transducer region, a common grouping pattern is set for a plurality of sub-arrays belonging to the transducer region, the amount of information related to the grouping pattern can be reduced as compared with a case where an individual grouping pattern is set for each of the plurality of sub-arrays. In addition, because a grouping pattern is set corresponding to each of the plurality of transducer regions, the precision of a beamforming, such as that used in converging, can be improved as compared with a case where a common grouping pattern is set over the entire array transducer.

With the present invention, an improved technique related to the grouping process of the array transducer is provided. For example, because, for each transducer region, a common grouping pattern is set for a plurality of sub-arrays belonging to the transducer region, the amount of information related to the grouping pattern can be reduced as compared with a case where an individual grouping pattern is set for each of the plurality of sub-arrays. In addition, because a grouping pattern is set corresponding to each of the plurality of transducer regions, the precision of the beamforming, such as that used in converging, can be improved as compared with a case where a common grouping pattern is set for the entire array transducer.

DESCRIPTION OF EMBODIMENT

A preferred embodiment of the present invention will now be described.

Figure 1:
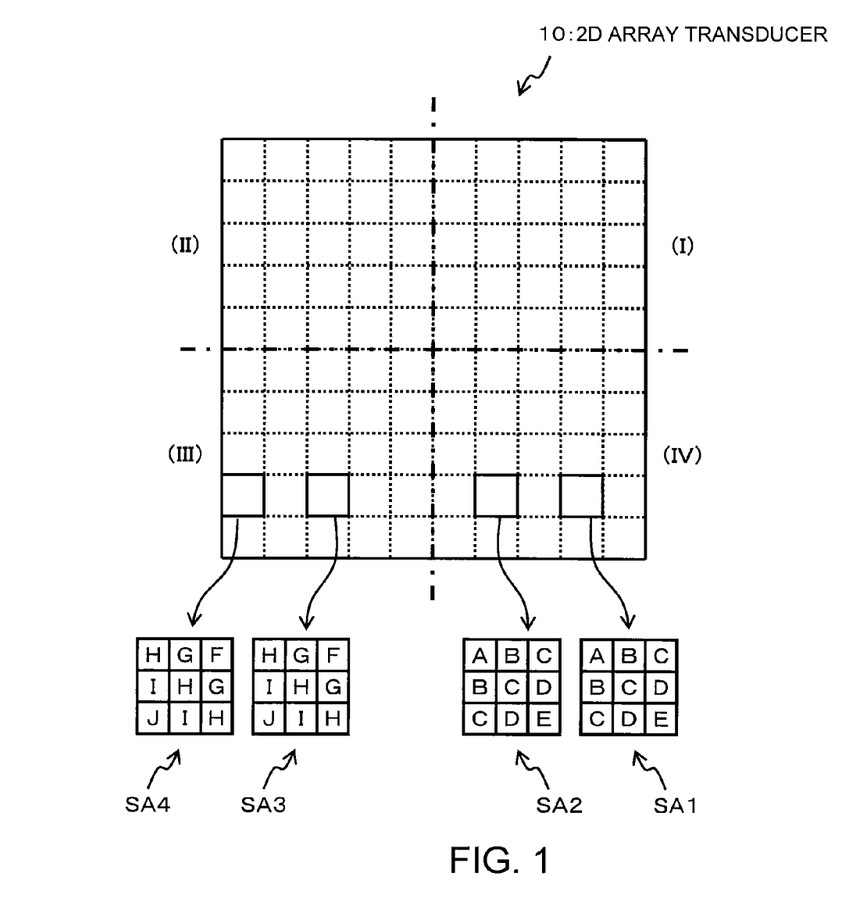
FIG. 1 is a diagram showing a 2D array transducer of an ultrasonic diagnostic apparatus of a preferred embodiment of the present invention.

FIG. 1 is a diagram showing a two-dimensional (2D) array transducer 10 of an ultrasonic diagnostic apparatus of a preferred embodiment of the present invention. The 2D array transducer 10 is formed by two-dimensionally arranging a plurality of transducer elements. For example, a plurality of transducer elements are two-dimensionally arranged in a vertical direction and a lateral direction, and a transducer surface of the 2D array transducer 10 is formed in a square shape as shown in FIG. 1. Alternatively, the plurality of transducer elements may be two-dimensionally arranged in a circular shape so that the transducer surface of the 2D array transducer 10 is formed into a circular shape.

The 2D array transducer 10 is divided into a plurality of sub-arrays. In FIG. 1, each of a plurality of squares separated in a lattice shape by a dotted line represents a sub-array. FIG. 1 shows in an enlarged manner four sub-arrays SA1-SA4 as representative sub-arrays. Each sub-array comprises a plurality of transducer elements. For example, each sub-array comprises nine transducer elements. In FIG. 1, nine squares arranged in a lattice shape in each of the sub-arrays SA1-SA4 represent nine transducer elements.

In addition, the 2D array transducer 10 is segmented into a plurality of transducer regions. In FIG. 1, four regions (I)-(IV) segmented by a dot-and-chain line represent four transducer regions. In FIG. 1, each of the transducer regions (I)-(IV) comprises 25 sub-arrays. It should be noted that FIG. 1 merely exemplifies one configuration for the preferred embodiment of the present invention, and the number of transducer elements in each sub-array and the number of sub-arrays in each transducer region are not limited to those shown in the example configuration of FIG. 1.

A plurality of transducer elements of the 2D array transducer 10 are electronically controlled, and, with this configuration, the ultrasound beam is two-dimensionally scanned and echo data are three-dimensionally collected. In the electronic control, an amount of delay (delay time) corresponding to each transducer element is set. For example, a transmitted signal which is delayed by the amount of delay corresponding to each transducer element is supplied to the transducer element, and a transmission beam is formed by a plurality of transducer elements of the 2D array transducer 10. In addition, for example, after the delay process by the amount of delay corresponding to each transducer element is applied to a reception signal obtained from the transducer element, the reception signals of a plurality of transducer elements of the 2D array transducer 10 are added, to form a reception signal along the reception beam.

In the present embodiment, in the formation of the ultrasound beam, a grouping process is applied based on a grouping pattern which sets a plurality of transducer elements corresponding to the same amount of delay in a same element group. In the grouping process, for each sub-array, a plurality of transducer elements belonging to the sub-array are grouped into a plurality of element groups. For each transducer region, a common grouping pattern is set for a plurality of sub-arrays belonging to the transducer region.

For example, because the sub-arrays SA1 and SA2 shown in FIG. 1 belong to the same transducer region (transducer region (IV)), a common grouping pattern is set for the sub-array SA1 and the sub-array SA2. In FIG. 1, the letters assigned to the transducer elements in the sub-arrays SA1 and SA2 indicate the group to which the transducer element belongs, and the same letter represents the same group. The arrangement pattern of the letters in the sub-array SA1 and the arrangement pattern of the letters in the sub-array SA2 match each other. In other words, the grouping pattern for the plurality of transducer elements in the sub-array SA1 and the grouping pattern for the plurality of transducer elements in the sub-array SA2 match each other.

Similarly, because the sub-arrays SA3 and SA4 shown in FIG. 1 belong to the same transducer region (transducer region (III)), a common grouping pattern is set for the sub-arrays SA3 and SA4.

In setting the common grouping pattern in each transducer region, a virtual infinity focus direction is set for each of the plurality of transducer regions based on an ideal focus position of the ultrasound beam, and a common grouping pattern is set for each transducer region according to the infinity focus direction which is set for each transducer region.

Figure 2:
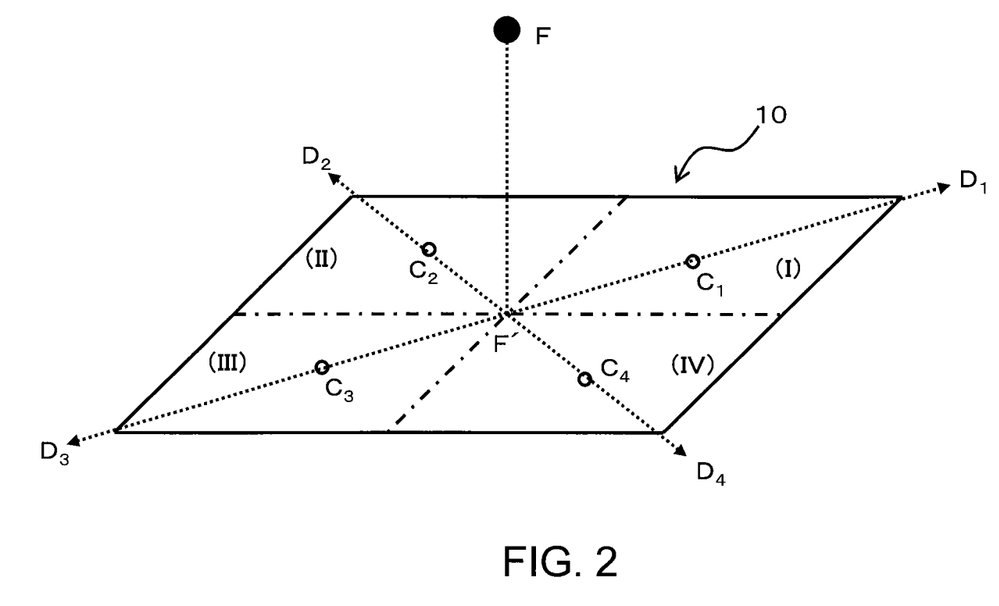
FIG. 2 is a diagram for explaining an infinity focus direction when there is no beam steering.

FIG. 2 is a diagram for explaining the infinity focus direction when there is no beam steering. FIG. 2 shows a square-shaped transducer surface of the 2D array transducer 10, and a focus point F of the ultrasound beam is present directly above the center of the transducer surface. A projected position of the focus point F on the transducer surface of the 2D array transducer 10 is a projected point F'.

When the infinity focus direction is set, a reference position is set in each transducer region according to an arrangement state of the plurality of transducer elements belonging to each transducer region. In FIG. 2, as the reference position, a position of a center of gravity C of each transducer region is set. In other words, a position of a center of gravity of a transducer surface formed by a plurality of transducer elements of the transducer region (I) is $C_1$, and, similarly, the position of the center of gravity of the transducer region (II) is $C_2$, the position of the center of gravity of the transducer region (III) is $C_3$, and the position of the center of gravity of the transducer region (IV) is $C_4$.

For each transducer region, an infinity focus direction is set along a straight line connecting the position of center of gravity C and the projected point F'. In other words, an infinity focus direction $D_1$ of the transducer region (I) is set along a straight line connecting the position of the center of gravity $C_1$ and the projected point F', an infinity focus direction $D_2$ of the transducer region (II) is set along a straight line connecting the position of the center of gravity $C_2$ and the projected point F', an infinity focus direction $D_3$ of the transducer region (III) is set along a straight line connecting the position of the center of gravity $C_3$ and the projected point F', and an infinity focus direction $D_4$ of the transducer region (IV) is set along a straight line connecting the position of the center of gravity $C_4$ and the projected point F'.

In addition, a common grouping pattern is set for each transducer region according to the infinity focus direction which is set for each transducer region.

Figure 3:
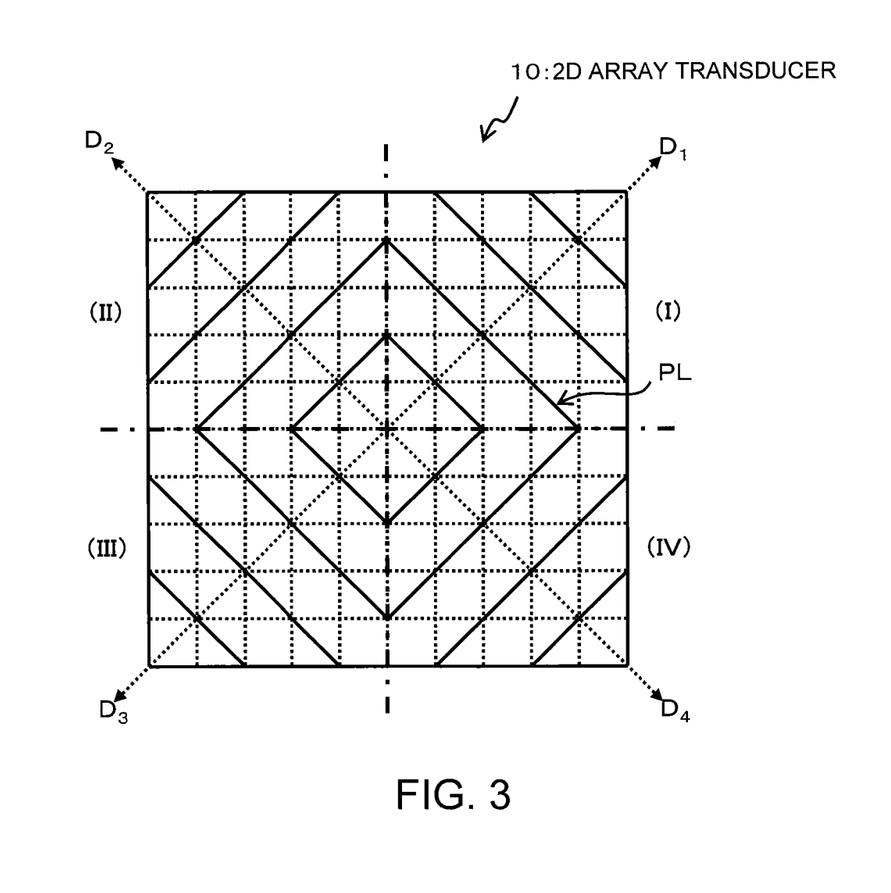
FIG. 3 is a diagram for explaining a common grouping pattern.

FIG. 3 is a diagram for explaining the common grouping pattern. FIG. 3 shows a square-shaped transducer surface of the 2D array transducer 10 identical to that of FIG. 1, and, in FIG. 3 also, each of the plurality of squares separated in a lattice shape by the dotted line represents a sub-array. In addition, FIG. 3 shows the infinity focus direction for each transducer region. In other words, FIG. 3 shows the infinity focus direction $D_1$ of the transducer region (I), the infinity focus direction $D_2$ of the transducer region (II), the infinity focus direction $D_3$ of the transducer region (III), and the infinity focus direction $D_4$ of the transducer region (IV).

For each transducer region, a contour line (delay equivalence line) related to the amount of delay is set based on the infinity focus direction. The delay equivalence line PL is a line connecting points of the same amount of delay when the ultrasound beam is formed, and is set to be orthogonal to the infinity focus direction. The position and spacing of the delay equivalence line PL shown in FIG. 3 are merely exemplary for the purpose of illustration, and the position and spacing of the delay equivalence line PL may be determined according to the positions and spacings of the plurality of transducer elements.

In the present embodiment, a plurality of transducer elements corresponding to the same amount of delay are grouped in a same element group. Thus, a plurality of transducer elements arranged along the delay equivalence line PL are grouped into the same element group. For example, in the transducer region (IV) in FIG. 3, the plurality of transducer elements are grouped along the delay equivalence line PL for each sub-array, so that a common grouping pattern such as the sub-array SA1 and the sub-array SA2 shown in FIG. 1 is formed. For the other transducer regions also, a plurality of transducer elements are grouped along the delay equivalence line PL, to form a common grouping pattern.

Figure 4:
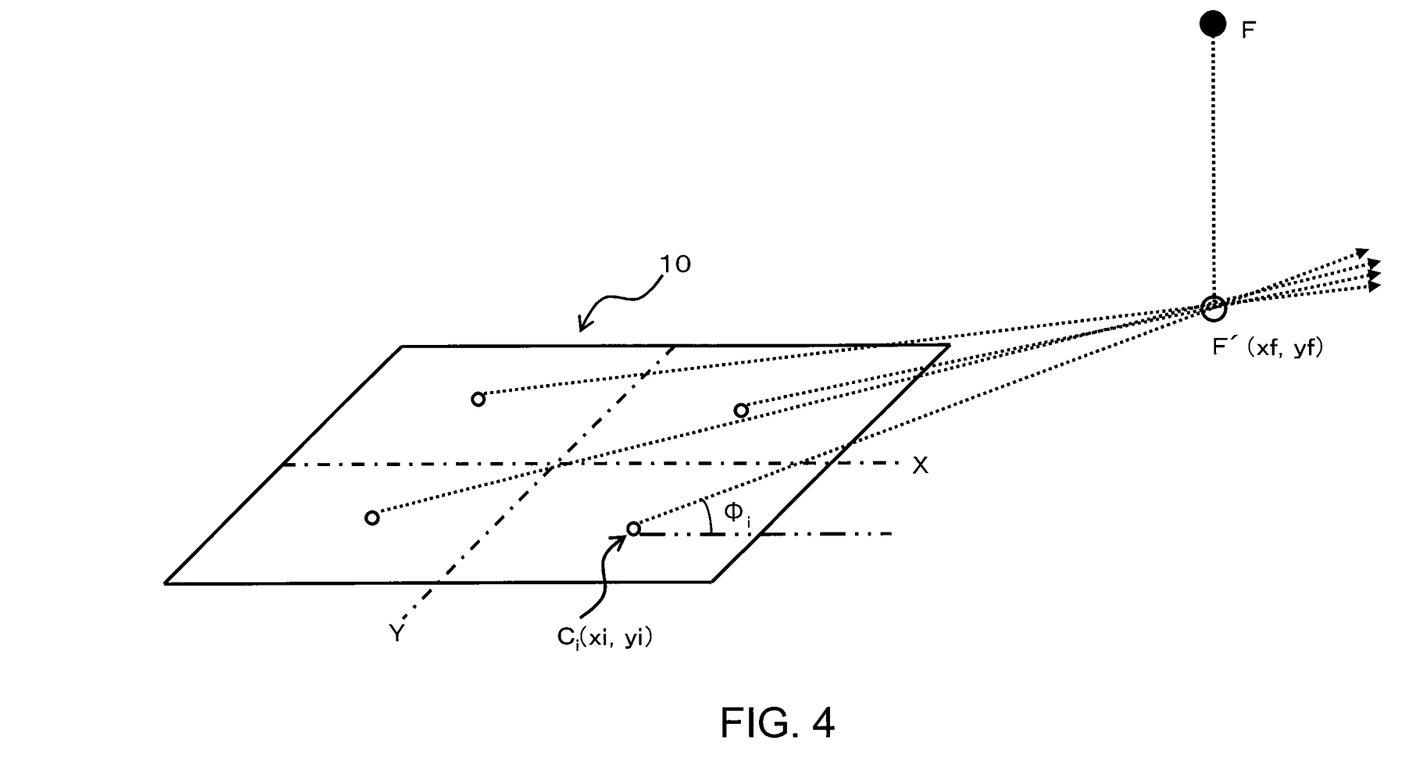
FIG. 4 is a diagram for explaining an infinity focus direction when there is beam steering.

FIG. 4 is a diagram for explaining an infinity focus direction when there is a beam steering. Also in the case where there is a beam steering, the infinity focus direction is set through a principle identical to that of the case where there is no beam steering (refer to FIG. 2).

FIG. 4 also shows a square-shaped transducer surface of the 2D array transducer 10. In FIG. 4, the focus point F of the ultrasound beam is present at a position distanced from the position directly above the transducer surface. In addition, a projected position of the focus point F on the plane including the transducer surface of the 2D array transducer 10 is a projected point F'.

In FIG. 4 also, the infinity focus direction is set along a straight line connecting the position of the center of gravity C and the projected point F' for each transducer region. In FIG. 4, the position of the center of gravity is represented as $C_i$.

When a coordinate of the projected point F' is (xf, yf) and the coordinate of the position of the center of gravity $C_i$ of each transducer region is (xi, yi), the infinity focus direction $\Phi_i$ (angle with respect to the x axis) of each transducer region is determined by the following equation.

[Equation 1]

$$\Phi i = \tan^{-1}[(yf-yi)/(xf-xi)] \quad i=1\sim4 \qquad (1)$$

For the purpose of explanation, infinity along the infinity focus direction $\Phi_i$ is called an ultra-far distance $D_\infty$, and, for example, if $D_\infty$=100 m, the infinity focus coordinate (Xi, Yi) is determined by the following equation.

[Equation 2]

$$Xi=xi+D_\infty \cos \Phi i \qquad (2a)$$

$$Yi=yi+D_\infty \sin \Phi i \qquad (2b)$$

When a contour line (a delay equivalence line) related to the amount of delay is set along a circumference of a concentric circle centered on the infinity focus coordinate (Xi, Yi), a delay equivalence line PL which is very close to a straight line orthogonal to the infinity focus direction $\Phi_i$ is set. Because of this, even in the case shown in FIG. 4 where there is beam steering, the delay equivalence line PL is set for each transducer region, in a manner to be orthogonal to the infinity focus direction $\Phi_i$.

Figure 5:
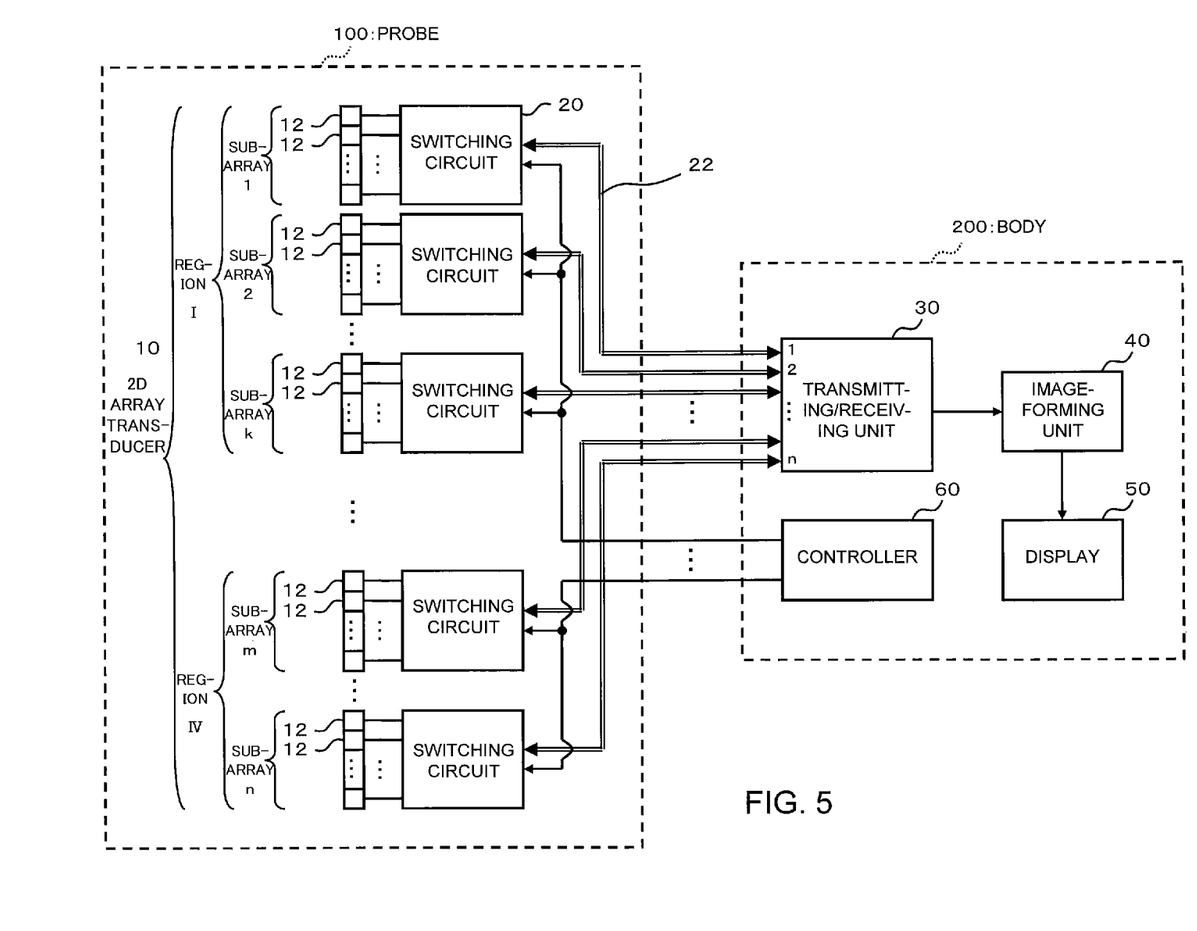
FIG. 5 is a diagram showing the overall structure of an ultrasonic diagnostic apparatus of the preferred embodiment of the present invention.

FIG. 5 is a diagram showing the overall structure of an ultrasonic diagnostic apparatus preferable in the present embodiment. The ultrasound diagnostic apparatus of FIG. 5 comprises a probe 100 and a body 200, and the probe 100 and the body 200 are connected to each other via a cable.

The probe 100 comprises the 2D array transducer 10 (refer to FIG. 1). The 2D array transducer 10 is constructed by two-dimensionally arranging a plurality of transducer elements 12. In addition, the 2D array transducer 10 is divided into a plurality of sub-arrays 1~n and segmented into a plurality of transducer regions I~IV.

A switching circuit 20 is provided for each of the plurality of sub-arrays 1~n. The switching circuit 20 executes a grouping process to group the plurality of transducer elements included in the corresponding sub-array into a plurality of element groups.

Each switching circuit 20 is, for example, a cross-point switch, and, in each switching circuit 20, a plurality of element signal lines corresponding to the plurality of transducer elements 12 and a plurality of group signal lines corresponding to a plurality of element groups are placed to cross each other. In FIG. 5, for each switching circuit 20, a group signal line bundle 22 comprising a plurality of group signal lines is shown.

In each switching circuit 20, a switch is provided at each crossing position where the signal lines cross, and, according to the switching ON/OFF of the switch, the element signal lines and the group signal lines are electrically connected to each other or electrically disconnected from each other, resulting in a grouping process. In the grouping process, a grouping pattern which is set for each sub-array is used.

The device body 200 comprises a transmitting/receiving unit 30. During transmission, the transmitting/receiving unit 30 outputs a transmitted signal to which a delay process is applied for each group, via the plurality of group signal lines included in the group signal line bundle 22, to each of the plurality of switching circuits 20. For each group, each switching circuit 20 then outputs the transmitted signal to the plurality of transducer elements 12 belonging to the group. In this manner, a transmitted signal to which the delay process is applied is supplied to the plurality of transducer elements 12 of the 2D array transducer 10, and the transmission beam is formed.

Meanwhile, upon reception, each switching circuit 20 groups the reception signals obtained from the plurality of transducer elements 12 to form a group signal, and outputs the resultant group signal via the plurality of group signal lines included in the group signal line bundle 22 to the transmitting/receiving unit 30. The transmitting/receiving unit 30 applies, on the group signal for each group obtained from each switching circuit 20, a delay process corresponding to the group, and adds the plurality of group signals after the delay process obtained from the plurality of switching circuits 20. In this manner, the reception signals obtained from the plurality of transducer elements 12 of the 2D array transducer 10 are summed and echo data along the reception beam are obtained.

An image-forming unit 40 forms image data based on echo data obtained along a plurality of reception beams. An ultrasound image corresponding to the image data is displayed on a display 50. For example, the ultrasound beam is two-dimensionally scanned and echo data are three-dimensionally collected, and a three-dimensional ultrasound image is formed. Alternatively, a two-dimensional ultrasound image may be formed.

A controller 60 integrally controls each unit of the ultrasonic diagnostic apparatus of FIG. 5. In particular, the controller 60 outputs control data for setting the grouping pattern to the plurality of switching circuits 20. The controller 60 may use a grouping pattern which is stored in a memory or the like in advance or may determine the grouping pattern through calculation based on the position of the focus point of the ultrasound beam or the like.

In the present embodiment, a common grouping pattern is set for a plurality of sub-arrays in each transducer region. Because of this, the controller 60 may output the same control data to the plurality of switching circuits 20 belonging to the same transducer region. For example, common control data are output to a plurality of switching circuits 20 belonging to the region I. Therefore, the controller 60 may output control data corresponding to the number of transducer regions (for example, four).

Figure 6:
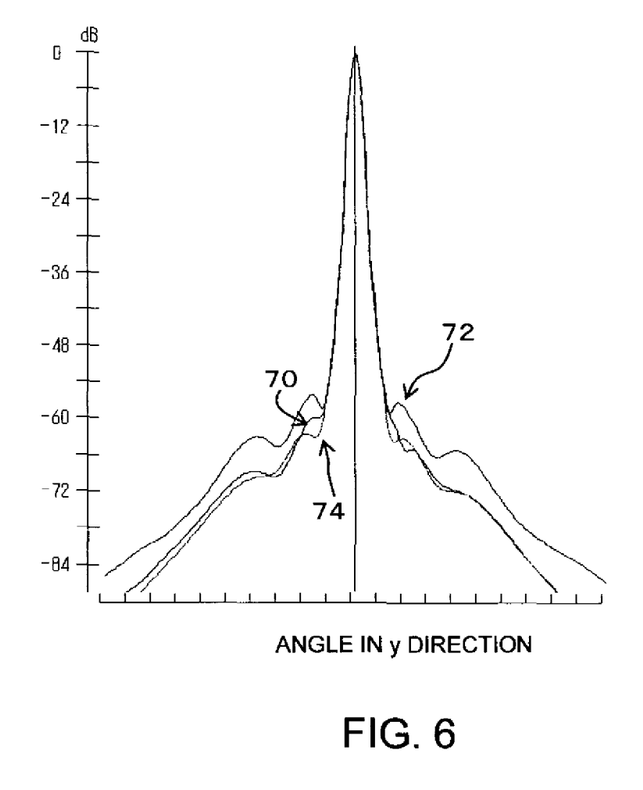
FIG. 6 is a diagram showing a comparison result related to precision of the beamforming.

FIG. 6 is a diagram showing a comparison result related to precision of the beamforming. FIG. 6 shows a beam characteristic in the y direction by a sound field simulation. The horizontal axis of FIG. 6 shows an angle in the y direction and the vertical axis represents intensity of the sound field.

FIG. 6 shows comparison results of three patterns related to the grouping process. A waveform 72 represents a sound field characteristic in a case where a common grouping pattern is used over the entire region of the 2D array transducer by setting the focus distance at infinity and considering only the steering. A waveform 74 represents a sound field characteristic when the grouping pattern is individually set for each sub-array over the entire region of the 2D array transducer.

A waveform 70, on the other hand, represents a sound field characteristic obtained by the present embodiment. In other words, the waveform 70 represents a sound field characteristic obtained when a common grouping pattern is set for a plurality of sub-arrays in each transducer region.

Upon comparison of the three patterns, it can be seen that there is no significant difference in the main lobe where the intensity of the sound field becomes the maximum. However, in the grating lobe deviated from the main lobe, a relatively significant difference arises among the three patterns.

In the beam characteristic, the grating lobe is desirably small. Of the three patterns, in the waveform 74, because the grouping pattern is individually set for each sub-array over the entire region of the 2D array transducer, the grating lobe is the smallest, and superior beamforming precision is achieved. In the waveform 72, because the beam control is a simplified control which uses a common grouping pattern over the entire region of the 2D array transducer, the grating lobe is the largest and the beamforming precision is inferior.

The waveform 70 which is the sound field characteristic resulting from the configuration of the present embodiment, on the other hand, has a smaller grating lobe as compared with the waveform 72, and the grating lobe is inhibited to a level very close to that of the waveform 74.

Because the grouping pattern is individually set for each sub-array in the waveform 74, a huge amount of information for the grouping pattern is required. On the other hand, in the waveform 70, which is the sound field characteristic resulting from the configuration of the present embodiment, because the only requirement is to set a common grouping pattern to the plurality of sub-arrays in each transducer region, the amount of information of the grouping pattern can be maintained at a low level. For example, if the individual grouping pattern is to be set for each of 164 sub-arrays, 164 grouping patterns would be required, but in the present embodiment, 4 grouping patterns corresponding to the 4 transducer regions may be set. In other words, the number of grouping patterns can be drastically reduced from 164 to 4.

As described, according to the present embodiment, the precision of the beamforming can be maintained while the number of grouping patterns is reduced.

As described above with reference to FIG. 3, when the grouping pattern is set in the present embodiment, a plurality of transducer elements arranged along the delay equivalence line PL are grouped into the same element group.

Figure 7:
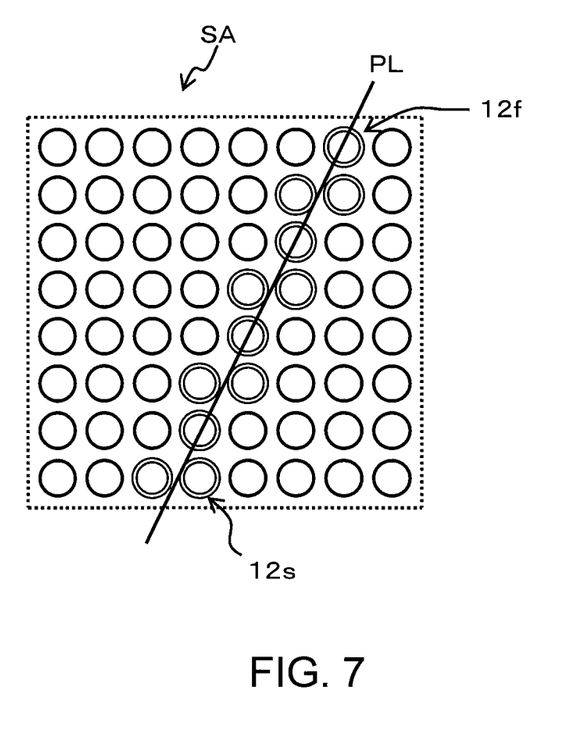
FIG. 7 is a diagram for explaining a relationship between a delay equivalence line PL and the element group.

FIG. 7 is a diagram for explaining a relationship between the delay equivalence line PL and the element group. FIG. 7 shows a sub-array SA having a square shape, shown with a dotted line. A plurality of circles included in the sub-array SA represent the plurality of the transducer elements. In the example configuration of FIG. 7, 8 transducer elements are arranged along the vertical direction and along the horizontal direction, and the sub-array SA is constructed with 64 transducer elements. For the sub-array SA, the delay equivalence line PL shown with a solid line is set, and a plurality of transducer elements are grouped into a same element group along the delay equivalence line PL.

When the delay equivalence line PL as shown in FIG. 7 is set, a plurality of transducer elements positioned on or near the delay equivalence line PL are grouped into the same element group. In FIG. 7, a plurality of transducer elements positioned on or near the delay equivalence line PL are shown with double circle marks. In other words, the plurality of transducer elements shown by these double circle marks are grouped into the same element group and correlated to the same amount of delay.

However, the plurality of transducer elements shown with the double circle mark include elements positioned on the delay equivalence line PL such as the transducer element 12*f* and elements deviated from the delay equivalence line PL such as the transducer element 12*s*. The delay equivalence line PL is ideally a line connecting points of the same amount of delay. Therefore, the transducer elements having different deviations from the delay equivalence line PL, for example, the transducer elements 12*f* and 12*s*, have, strictly speaking, different amounts of delay.

In consideration of this, the amount of delay may be finely adjusted for each transducer element according to the deviation from the delay equivalence line PL. For example, a fine adjustment circuit of the amount of delay may be inserted between the transducer elements 12 shown in FIG. 5 and the switching circuit 20, and the amount of delay may be finely adjusted for each transducer element 12 according to the deviation from the delay equivalence line PL. Upon reception, the reception signals obtained from the plurality of transducer elements 12 are grouped into a group signal after the amount of delay is finely adjusted, and, in the transmission, the transmitted signal corresponding to each group is transmitted to each transducer element 12 after the amount of delay is finely adjusted according to each transducer element 12. By finely adjusting the amount of delay for each transducer element 12, the precision of the ultrasound beamforming can be further improved.

Figure 8:
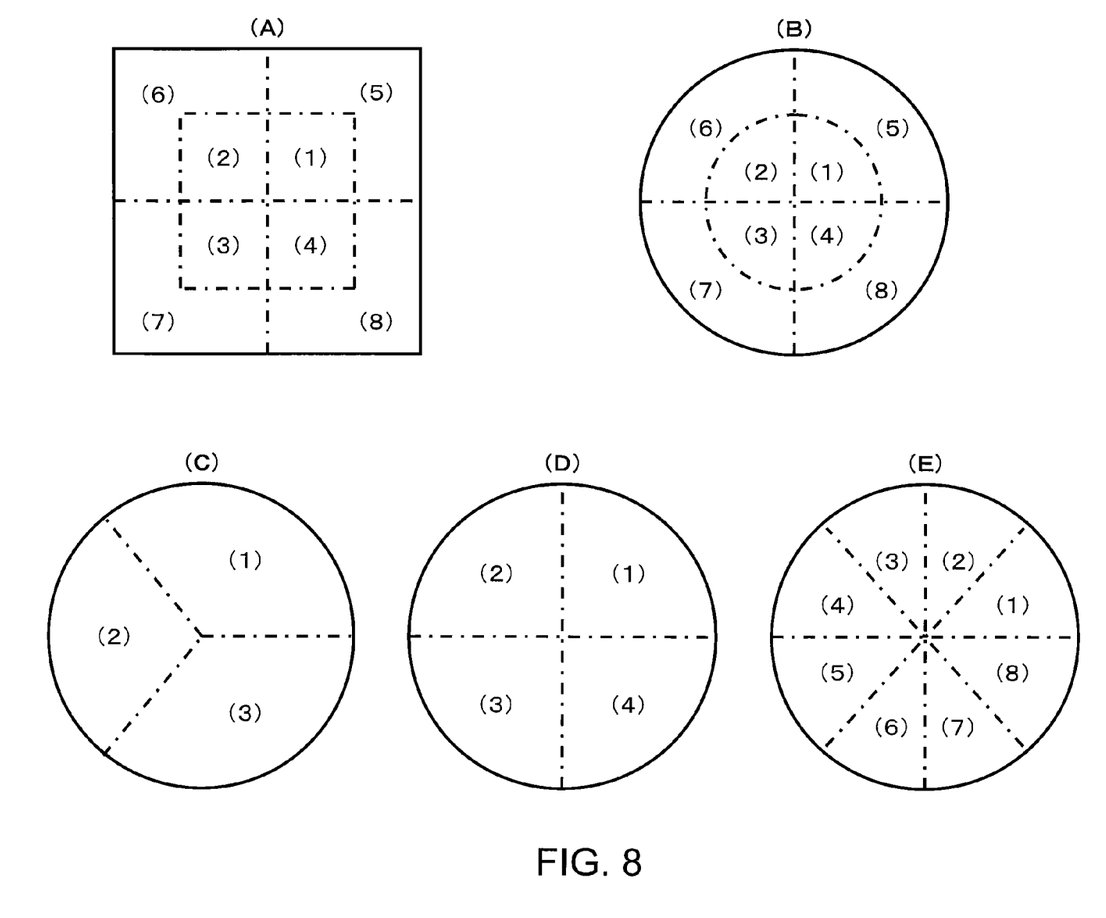
FIG. 8 is a diagram showing various segmenting patterns of the transducer region.

FIG. 8 is a diagram showing various segmenting patterns of the transducer regions. In each of patterns (A)-(E), a square or a circle surrounded by solid lines represents a transducer surface of the 2D array transducer, and a dot-and-chain line drawn within the transducer surface represents a boundary of the transducer region.

The 2D array transducer is segmented into a plurality of transducer regions by a virtual boundary extending radially from the center of the transducer surface, and is further segmented, as necessary, into a plurality of transducer regions by a virtual boundary which is set to surround the center of the transducer surface.

In pattern (A), a square transducer surface is segmented into 8 transducer regions (1)-(8). In pattern (B), a circular transducer surface is segmented into 8 transducer regions (1)-(8). In addition, patterns (C)-(E) show example segmenting patterns for a circular transducer surface.

As described, various segmenting patterns can be employed for the transducer regions, and segmenting patterns other than the segmenting patterns shown in FIGS. 1 and 8 may be used.

A preferred embodiment of the present invention has been described. However, it should be noted that the above-described preferred embodiment is merely exemplary and does not limit the scope of the present invention.

What is claimed is:

1. An ultrasonic diagnostic apparatus comprising:
an array transducer comprising a plurality of transducer elements;
a grouping processor which divides the array transducer into a plurality of sub-arrays and which groups, for each sub-array, a plurality of transducer elements belonging to the sub-array into a plurality of element groups;
a controller which sets a grouping pattern defining a plurality of transducer elements to be grouped into a same element group; and
a beam-forming unit which forms an ultrasound beam using a plurality of element groups grouped for each sub-array over the plurality of sub-arrays, wherein
the array transducer is segmented into a plurality of transducer regions,
for each of the transducer regions, the controller is configured to set a common grouping pattern for those of the plurality of sub-arrays belonging to each of the segmented transducer regions, and
the controller is configured to set the common grouping pattern for each transducer region by setting a virtual infinity focus direction for each of the plurality of transducer regions based on an ideal focus position of an ultrasound beam, by setting, for each transducer region, a delay equivalence line which is a straight line orthogonal to the infinity focus direction, and by grouping a plurality of transducer elements arranged along the delay equivalence line into the same element group.

2. The ultrasonic diagnostic apparatus according to claim 1, wherein
the controller sets the grouping pattern such that a plurality of transducer elements corresponding to a same amount of delay during formation of an ultrasound beam are grouped into a same element group.

3. The ultrasonic diagnostic apparatus according to claim 2, wherein
the controller is configured to set a reference position in each transducer region according to an arrangement state of the plurality of transducer elements belonging to the transducer region, and the infinity focus direction for each transducer region along a straight line connecting a projected position of the ideal focus position on an array transducer surface and the reference position of the transducer region.

4. The ultrasonic diagnostic apparatus according to claim 3, wherein
the controller is configured to set the reference position in each transducer region which is a position of a center of gravity of the transducer region.

5. The ultrasonic diagnostic apparatus according to claim 2, wherein
the grouping processing having a fine adjustment circuit to finely adjust an amount of delay for each transducer element according to a deviation from the delay equivalence line connecting points of a same amount of delay when an ultrasound beam is formed.

6. The ultrasonic diagnostic apparatus according to claim 3, wherein
the grouping processor having a fine adjustment circuit to finely adjust an amount of delay for each transducer element according to a deviation from the delay equivalence line connecting points of a same amount of delay when an ultrasound beam is formed.

7. The ultrasonic diagnostic apparatus according to claim 1, wherein
the controller is configured to finely adjust an amount of delay for each transducer element according to a deviation from the delay equivalence line connecting points of a same amount of delay when an ultrasound beam is formed.

8. The ultrasonic diagnostic apparatus according to claim 7, wherein
the array transducer is a two-dimensional array transducer comprising a plurality of transducer elements which are two-dimensionally arranged.

9. The ultrasonic diagnostic apparatus according to claim 1, wherein
the grouping processor having a fine adjustment circuit to finely adjust an amount of delay for each transducer element according to a deviation from the delay equivalence line connecting points of a same amount of delay when an ultrasound beam is formed.

10. The ultrasonic diagnostic apparatus according to claim 1, wherein
the array transducer is a two-dimensional array transducer comprising a plurality of transducer elements which are two-dimensionally arranged.

11. The ultrasonic diagnostic apparatus according to claim 10, wherein
the controller is configured to segment the two-dimensional array transducer into the plurality of transducer regions by a virtual boundary extending out from a center of a transducer surface.

12. The ultrasonic diagnostic apparatus according to claim 11, wherein
the controller is configured to further segment the two-dimensional array transducer into the plurality of transducer regions by a virtual boundary which is set to surround a center of the transducer surface.

13. The ultrasonic diagnostic apparatus according to claim 12, wherein
the controller is configured to segment the two-dimensional array transducer into three or more transducer regions.

14. The ultrasonic diagnostic apparatus according to claim 10, wherein
the controller is configured to segment the two-dimensional array transducer into three or more transducer regions.

* * * * *